US011752133B2

(12) United States Patent
Shi et al.

(10) Patent No.: US 11,752,133 B2
(45) Date of Patent: *Sep. 12, 2023

(54) USE OF BROMOPHENOL-PYRAZOLINE COMPOUNDS IN THE TREATMENT OF PORCINE CORONAVIRUS DISEASES

(71) Applicant: Shandong Linghai Biotechnology Co., Ltd., Weihai (CN)

(72) Inventors: Dayong Shi, Rongcheng (CN); Xiangqian Li, Rongcheng (CN); Xin Wang, Rongcheng (CN); Jinbo Yang, Rongcheng (CN); Feng Xu, Rongcheng (CN); Rong Zhang, Rongcheng (CN)

(73) Assignee: SHANDONG LINGHAI BIOTECHNOLOGY CO., LTD., Weihai (CN)

( * ) Notice: Subject to any disclaimer, the term of this patent is extended or adjusted under 35 U.S.C. 154(b) by 57 days.

This patent is subject to a terminal disclaimer.

(21) Appl. No.: 17/478,134

(22) Filed: Sep. 17, 2021

(65) Prior Publication Data

US 2022/0193036 A1 Jun. 23, 2022

(30) Foreign Application Priority Data

Dec. 18, 2020 (CN) .......................... 202011506016.1

(51) Int. Cl.
*A61K 31/415* (2006.01)
*A61P 31/14* (2006.01)
(Continued)

(52) U.S. Cl.
CPC .......... *A61K 31/415* (2013.01); *A61K 31/427* (2013.01); *A61K 31/428* (2013.01); *A61P 31/14* (2018.01)

(58) Field of Classification Search
CPC .... A61P 31/14; A61P 1/16; A61P 3/10; A61P 31/12; A61P 5/50; G01N 33/582; G01N 33/533; G01N 33/545; G01N 2458/30; G01N 33/5005; G01N 33/581; G01N 33/585; G01N 33/587; G01N 33/6872; C07D 471/04; C07D 487/04; C07D 307/85; C07D 405/12; C07D 231/06; C07D 239/94; C07D 475/06; C07D 487/14; C07D 495/04; C07D 513/04; C07D 519/00; C07D 417/04; C07F 7/0816; C07F 7/083; C08G 2261/122; C08G 2261/124;
(Continued)

(56) References Cited

FOREIGN PATENT DOCUMENTS

CN 106496123 * 3/2017 ........... C07D 231/06

OTHER PUBLICATIONS

English translation of the Chinese patent CN 106496123 (Year: 2017).*

* cited by examiner

*Primary Examiner* — Savitha M Rao (57) ABSTRACT

The invention belongs to the technical field of medicine, and particularly relates to use of bromophenol-pyrazoline compounds in the treatment of porcine coronavirus diseases. Through the research in the invention, it is found that the bromophenol-pyrazoline compounds inhibit replication of porcine coronaviruses at a cellular level, and can treat porcine coronavirus diseases (such as PEDV and TGEV) in clinical trials, greatly improving the survival rate of infected piglets, so the compounds can be used to prepare drugs for treating porcine coronavirus diseases.

3 Claims, 3 Drawing Sheets (51) Int. Cl.
*A61K 31/428* (2006.01)
*A61K 31/427* (2006.01)

(58) Field of Classification Search
CPC ...... C08G 2261/1424; C08G 2261/145; C08G 2261/1644; C08G 2261/1646; C08G 2261/3142; C08G 2261/3244; C08G 2261/334; C08G 2261/344; C08G 2261/411; C08G 2261/522; C08G 2261/5222; C08G 2261/72; C08G 2261/94; C08G 61/123; C08L 65/00; C09K 11/06; C09K 2211/1416; C09K 2211/1491; H10K 85/115; H10K 85/151; H10K 85/40; A61K 38/00; A61K 45/06; A61K 31/075; A61K 31/09; A61K 31/12; A61K 31/415; A61K 31/428; A61K 31/427; C07C 41/09; C07C 41/18; C07C 41/22; C07C 41/26; C07C 41/30; C07C 43/1786; C07C 43/225; C07C 43/23; C07C 45/455; C07C 45/46; C07C 45/63; C07C 49/84; C07C 51/16; C07C 65/21; C12Q 1/6883; C12Q 1/6816; C12Q 1/6818; C12Q 2563/103; C12Q 2563/125; C12Q 2563/155; C12Q 2565/101; C12Q 2600/106; C12Q 2600/136; C12Q 2600/153; C12Q 2600/172

See application file for complete search history.

USE OF BROMOPHENOL-PYRAZOLINE COMPOUNDS IN THE TREATMENT OF PORCINE CORONAVIRUS DISEASES

FIELD OF THE INVENTION

The invention belongs to the technical field of medicine, and relates to a new use of bromophenol-pyrazoline compounds, especially use of bromophenol-pyrazoline compounds in the treatment of porcine coronavirus diseases.

BACKGROUND OF THE INVENTION

Porcine coronaviruses (PEDV, TGEV, PDCoV, etc.) are highly contagious and associated with serious diseases such as diarrhea and vomiting, and increase the mortality rate of piglets (generally 100%). Such coronaviruses can cause sporadic outbreaks (endemic) or large-scale epidemics in pig-raising countries, are characterized by acute onset, high infectivity and high mortality rate, and have caused serious economic losses to the pig industry in Asia, Europe and the Americas. Since October 2010, a series of large-scale porcine epidemic diarrhea virus (PEDV) epidemics have also occurred in China, causing huge economic losses of up to hundreds of billions of RMB.

In 2010, the incidence of porcine epidemic diarrhea (PED) increased significantly. According to the sampling and analysis by experts, this epidemic diarrhea virus was a mutant strain, which was mainly mutated in bats, and the virulence of the mutated virus increased significantly. For pig herds, porcine epidemic diarrhea (PED) is the most serious hazard to suckling piglets, with a mortality rate close to 100%. Although vaccines (for the prototype PEDV strain CV777) were tried, the effect was not obvious due to the existence of multiple mutant strains for PEDV. For example, 15 new wild PEDV mutants were detected in manure or intestinal samples of pigs with diarrhea collected from December 2013 to June 2015.

Porcine transmissible gastroenteritis virus (TGEV) is also a member of the Coronavirus genus of the Coronaviridae family, and the transmissible gastroenteritis caused thereby no less harmful than epidemic diarrhea (PEDV). This virus was first reported in the U.S. in 1946, and soon rapidly spread throughout the world. The epidemic situation of TGE is severe in China. Pigs of various ages can be 100% infected with this disease in a short period of time, and are often accompanied by mixed infection of porcine epidemic diarrhea (PED). The disease condition varies with days of age, the mortality rate is higher when the days of age is smaller, and the mortality rate of the piglets within 2 weeks of age is up to 90-100%.

At present, there is no effective drug available for porcine coronaviruses in the international and domestic markets. Except for the use of vaccination for early prevention (there is no vaccine with a specific immune effect), only the conservative treatment with traditional Chinese medicine and antibodies can be used, but due to the continuous mutation of strains, the virulence continues to increase, showing increasing killing power, so the effect of traditional Chinese medicine and antibody treatment is undesirable.

Bromophenol-pyrazoline compounds are compounds with the activity of inhibiting novel coronaviruses designed by the inventor in the early stage of research and development, which have broad application prospects in the preparation of drugs for treating human coronavirus pneumonia. Therefore, bromophenol-pyrazoline compounds are a class of compounds with great medicinal potential, and it will be of great significance to further discover their new medicinal effects.

SUMMARY OF THE INVENTION

In view of the above prior art, an object of the invention is to provide a new medical use of bromophenol-pyrazoline compounds. Through the research in the invention, it is found that the bromophenol-pyrazoline compounds can inhibit replication of porcine coronaviruses (such as PEDV and TGEV) at a cellular level, and can treat porcine coronavirus diseases (such as PED and TGE) in clinical trials, greatly improving the survival rate of infected piglets, so the compounds can be used to prepare drugs for treating porcine coronavirus diseases.

To achieve the above object, the invention employs the following technical solutions. A first aspect of the invention provides use of bromophenol-pyrazoline compounds in the preparation of drugs for treating porcine coronavirus diseases.

In the use, the bromophenol-pyrazoline compounds have a general structural formula shown in the following formula I:

in which, $R_1$, $R_2$, $R_3$, $R_4$ and $R_5$ are respectively selected from any one of H, F, Br, OH and $OCH_3$;

$R_6$ is selected from any one of H, CHO, $COCH_3$, $COCH_2CH_3$, $COCH_2CH_2CH_3$, $COOCH_3$, $COOCH_2CH_3$, Ph, $CH_2Ph$, $CONH_2$, $CSNH_2$ or and $R_7$, $R_8$ and $R_9$ are respectively selected from any one of H, Br, $NO_2$, OH, $CH_3$, $OCH_3$ or $R_{10}$, $R_{11}$ and $R_{12}$ are respectively selected from any one of H, Br, $NO_2$, OH, $CH_3$, $C_2H_5$, $OCH_3$, $OC_2H_5$, isopropyl, isobutyl, tert-butyl and tert-amyl.

Preferably, the bromophenol-pyrazoline compound is any one of the following compounds:

In the use, the porcine coronavirus diseases are diseases such as gastroenteritis, diarrhea, respiratory inflammation and encephalomyelitis caused by porcine coronaviruses including but not limited to porcine transmissible gastroenteritis virus (TGEV), porcine epidemic diarrhea virus (PEDV), porcine respiratory coronavirus (PRCV), porcine deltacoronavirus (PDCoV), porcine hemagglutinating encephalomyelitis virus (PHEV), etc.

A second aspect of the invention provides a drug for treating porcine coronavirus diseases, wherein the drug comprises an effective amount of the bromophenol-pyrazoline compounds of claim 1 as an active ingredient.

Further, if necessary, one or more pharmaceutically acceptable carriers may also be added to the drug; and the carriers include conventional diluents, excipients, fillers, adhesives, wetting agents, disintegrants, absorption enhancers, surfactants, adsorption carriers, lubricants and the like in the pharmaceutical field.

Further, one of the bromophenol-pyrazoline compounds or a mixture of more than two thereof, and a pharmaceutically acceptable drug carrier can be mixed to prepare a tablet, a capsule, an oral liquid, a granule, a pill or an injection or the like for preventing and/or treating porcine coronavirus diseases.

A third aspect of the invention provides a method for treating diseases caused by porcine coronavirus infection, comprising the step of:

administering an effective amount of the bromophenol-pyrazoline compound shown in formula I to a recipient animal to treat diseases caused by viral infection.

The beneficial effects of the invention are as follows:

through the first research in the invention, it is found that the bromophenol-pyrazoline compounds have good inhibitory activity against porcine coronaviruses and can inhibit replication of porcine coronaviruses; and clinical trials have proved that the bromophenol-pyrazoline compounds can treat porcine coronavirus diseases caused by PEDV, TGEV, etc., thus greatly improving the survival rate of infected piglets.

DETAILED DESCRIPTION OF THE INVENTION

Figure 1:
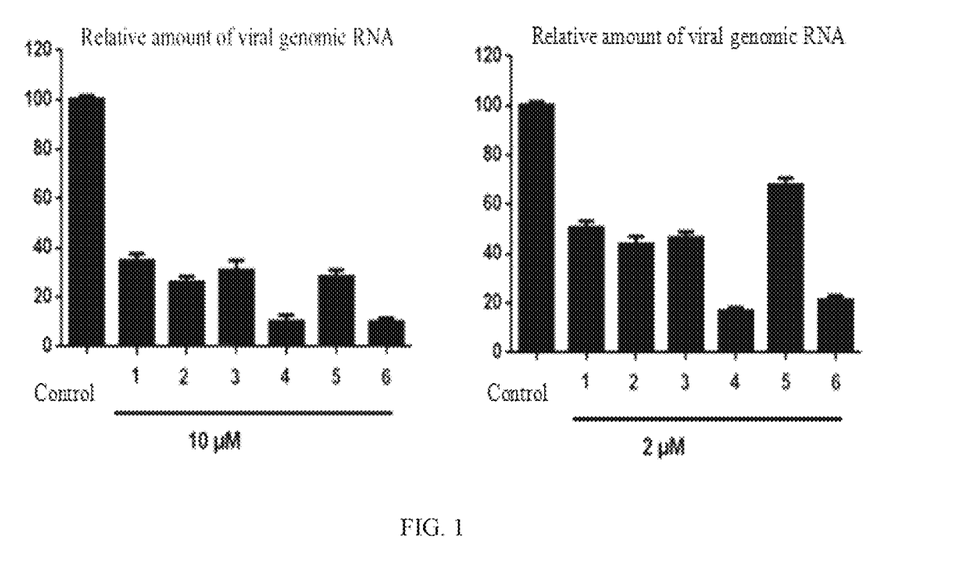
FIG. 1 shows the assay results of the inhibition of replication of porcine epidemic diarrhea virus (PEDV) in cells by compounds 1-6 provided in the examples of the invention so as to evaluate the effect of different concentrations of the compounds on viral RNA replication.
Figure 2:
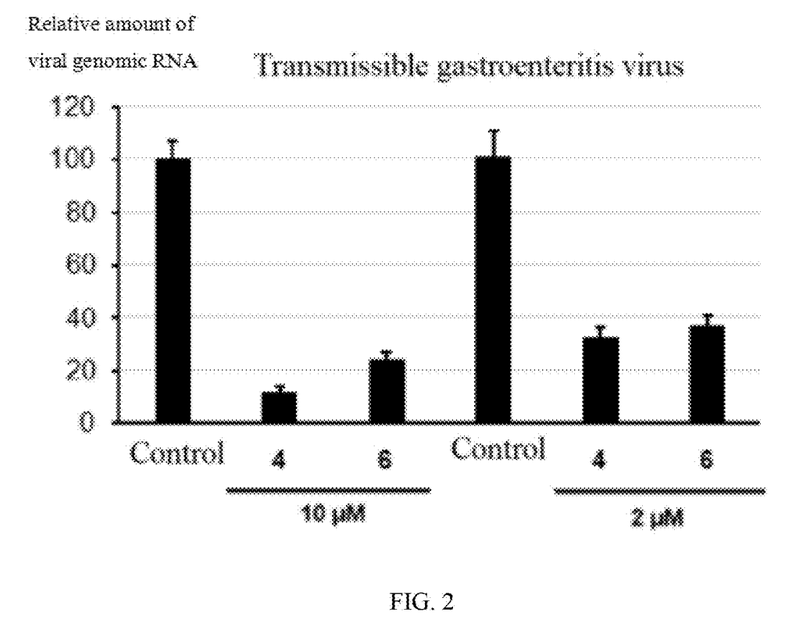
FIG. 2 shows the assay results of the inhibition of replication of porcine transmissible gastroenteritis virus (TGEV) in cells by compounds 4 and 6 provided in the examples of the invention so as to evaluate the effect of different concentrations of the compounds on viral RNA replication.
Figure 3:
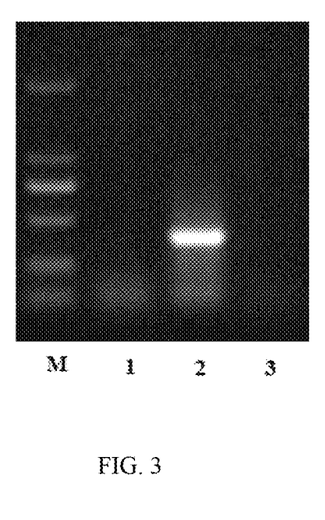
FIG. 3 shows the PCR detection of diseased pig tissues. In the figure, lanes 1 to 3 respectively represent TGEV (transmissible gastroenteritis virus), PEDV (porcine epidemic diarrhea virus) and PGAR (porcine group A rotavirus) in diseased pig tissue samples; and M represents DNA Marker.

For better understanding of the invention, the invention will be described below in more detail with reference to the drawings and particular examples. Preferred examples of the invention are given in the particular examples. However, the invention can be implemented in many different forms and is not limited to the examples described in the present description. On the contrary, the purpose of providing these examples is to allow a more thorough and comprehensive understanding of the disclosure of the invention.

It should be noted that the following detailed descriptions are all illustrative and are intended to provide further explanations for the present application. Unless otherwise specified, all technical and scientific terms used herein have the same meaning as commonly understood by those of ordinary skill in the art of the present application. As described in the background art, porcine coronavirus diseases have caused serious economic losses to the pig industry, but currently there are no effective therapeutic drugs against porcine coronaviruses.

Coronaviruses (CoVs) are a class of enveloped single-stranded RNA viruses, which are also currently known as RNA viruses with the largest genome size, and belong to the Coronavirus genus of the Coronaviridae family of the Nidovirales order. The viruses can cause respiratory, digestive and nervous system diseases in animals, mainly infecting humans and vertebrates.

There are many types of porcine coronaviruses, mainly porcine epidemic diarrhea virus (PEDV) and porcine transmissible gastroenteritis virus (TGEV) of the alphacoronavirus genus, which mainly cause piglet diarrhea; and porcine hemagglutinating encephalomyelitis virus (PHEV) of the betacoronavirus genus, which mainly causes digestive or nervous system symptoms in piglets.

In response to the outbreak of the novel coronavirus pneumonia epidemic at the end of 2019, the inventors developed a bromophenol-pyrazoline compound that can effectively inhibit the novel coronavirus (COVID-19), which has the effect of treating coronavirus pneumonia (see Chinese Patent Application No. CN111848516A for details).

However, the novel coronavirus (COVID-19) is a human-borne coronavirus, although there are a large variety of coronaviruses that exist widely, the coronaviruses usually have the highest affinity for a receptor of a natural host and have obvious species specificity for an infected host. At present, there is no mutual infection between human-borne coronaviruses and porcine coronaviruses. Moreover, the homology alignment between the genome sequence of the human novel coronavirus (SARS-CoV-2) collected from the GenBank database and those of porcine coronaviruses demonstrated that the evolutionary relation between porcine epidemic diarrhea virus (PEDV) and porcine transmissible gastroenteritis virus (TGEV), and SARS-CoV-2 is relatively long, and the genome homology is only 42.8%-43.5% (see "Genetic analysis on the homology between severe acute respiratory syndrome coronavirus 2 (SARS-CoV-2) and common domestic animal coronaviruses").

It follows that porcine coronaviruses and human novel coronaviruses have low homology, are distantly related, and also cause completely different conditions. Therefore, porcine coronaviruses and human novel coronaviruses belong to two different types of viruses, so it is rather difficult to predict the effect of substances that can inhibit human novel coronaviruses on porcine coronaviruses.

In order to further expand the medicinal field of bromophenol-pyrazoline compounds, a great deal of attempts have been conducted in the invention. As a result, it is found unexpectedly that the bromophenol-pyrazoline compounds have good inhibitory activity against porcine coronaviruses and can inhibit replication of porcine coronaviruses; and clinical trials have proved that the bromophenol-pyrazoline compounds can treat porcine coronavirus diseases caused by PEDV, TGEV, etc., thus greatly improving the survival rate of infected piglets. Therefore, the invention is proposed.

In order that those skilled in the art can understand the technical solutions of the present application more clearly, the technical solutions of the present application will be described in detail below in conjunction with particular examples.

All the unspecified test materials used in the examples of the invention are conventional test materials in the field, which can be commercially available.

The structural formulas of compounds 1-6 are shown below:

The compounds 1-6 can be prepared with reference to the method described in Chinese Patent Application (CN111848516A). The reaction process is as follows (taking compounds 4 and 6 as examples):

Example 1: Interference with Replication of Porcine Epidemic Diarrhea Virus (PEDV) in Cells by Bromophenol-Pyrazoline Compounds This Example evaluated whether bromophenol-pyrazoline compounds can inhibit replication of porcine coronavirus in Vero E6 cells infected with clinically isolated strains of porcine epidemic diarrhea virus (PEDV).

Specific operation: pre-seeded Vero E6 cells ($5\times10^4$ cells/well) were respectively pretreated for 1 h with different concentrations of bromophenol-pyrazoline compounds to be tested (2 μM and 10 μM), and then infected with porcine coronavirus (PEDV; MOI: 0.05) for 2 h. Then, a virus-compound mixture was removed, and the cells were further cultured with a fresh medium containing the bromophenol-pyrazoline compound. After 24 hours, a cell supernatant was collected, and vRNA in the supernatant was analyzed by qRT-PCR. The treatment without a bromophenol-pyrazoline compound was used as a control.

Experimental results: as shown in FIG. 1, in the Vero cells infected with porcine epidemic diarrhea virus (PEDV), the compounds with concentrations of 10 μM and 2 μM exhibited strong antiviral effects, wherein the compound 4 exhibited the strongest inhibitory activity against replication of the porcine coronavirus (FIG. 1).

Example 2: Interference with Replication of Porcine Transmissible Gastroenteritis Virus (TGEV) in Cells by Bromophenol-Pyrazoline Compounds This Example evaluated whether bromophenol-pyrazoline compounds can inhibit replication of porcine coronavirus in Vero E6 cells infected with clinically isolated strains of porcine transmissible gastroenteritis virus (TGEV).

Specific operation: pre-seeded Vero E6 cells ($5\times10^4$ cells/well) were respectively pretreated for 1 h with different concentrations of bromophenol-pyrazoline compounds to be tested (2 μM and 10 μM), and then infected with porcine coronavirus (TGEV; MOI: 0.05) for 2 h. Then, a virus-compound mixture was removed, and the cells were further cultured with a fresh medium containing the bromophenol-pyrazoline compound. After 24 hours, a cell supernatant was collected, and vRNA in the supernatant was analyzed by qRT-PCR. The treatment without a bromophenol-pyrazoline compound was used as a control.

Experimental results: as shown in FIG. 2, in the Vero cells infected with porcine transmissible gastroenteritis virus (TGEV), the compounds with concentrations of 10 μM and 2 μM exhibited strong antiviral effects, wherein the compound 4 exhibited the strongest inhibitory activity against replication of the porcine coronavirus (FIG. 2).

Example 3: Clinical Trial of Compound 4 in the Treatment of Diseased Pigs Infected with Porcine Epidemic Diarrhea Virus 1. PCR Detection of Viral Infection of Diseased Pigs Through the PCR detection of diseased pig tissues at Zhucheng Pig Farm in November 2020, the type of viral infection was determined. The PCR results (FIG. 3) showed that, PEDV (porcine epidemic diarrhea virus) was detected in diseased pig tissue samples, but no transmissible gastroenteritis virus and rotavirus were detected.

2. Clinical Trial of Compound 4 in the Treatment of Diseased Pigs with Epidemic Diarrhea Diseased pigs with epidemic diarrhea within 10 days of age were selected and randomly divided into 4 groups, i.e. untreated group, traditional Chinese medicine treatment group, compound 4 treatment group and lgY antibody treatment group, respectively. The traditional Chinese medicine treatment group was drenched with a compound decoction consisting of dandelion, Chinese violet, coptis, isatis root, etc., twice a day for 3 consecutive days. Compound 4 was taken at a dose of 25 mg/pig after being dissolved in a dextrose solution, twice a day. The lgY antibody treatment group was fed with chicken egg antibodies (lgY), twice a day. The untreated group, the traditional Chinese medicine treatment group and the lgY antibody treatment group were respectively drenched with the same dose of the glucose solution as the compound 4 treatment group. The pigs were breast-fed during treatment.

3. Clinical Trial Results:

(1) Clinical Treatment Results of Diseased Pigs with Epidemic Diarrhea

The clinical treatment results of diseased pigs with epidemic diarrhea are shown in Table 1. It can be seen from Table 1 that compound 4 has a significant effect on the treatment of diseased pigs with epidemic diarrhea, wherein the mortality rate is much lower than that of the other three groups and the effective rate is 100%. In the untreated group, 10 pigs died, with a mortality rate of 90.9%; in the traditional Chinese medicine treatment group, 9 pigs died, with a mortality rate of 75% and an effective rate of 25%; in the compound 4 treatment group, no pig died, with a mortality rate of 0% and an effective rate of 100%; and in the lgY antibody group, 5 pigs died, with a mortality rate of 83.3% and an effective rate of 16.7%.

TABLE 1

Data Summarization of Clinical Trials for Epidemic Diarrhea

| | Total | Number of deaths | Mortality rate | Effective rate |
|---|---|---|---|---|
| Untreated group | 11 (6 + 5) | 10 | 90.9% | NA |
| Traditional Chinese medicine treatment group | 12 (6 + 6) | 9 | 75.0% | 25.0% |
| Compound 4 treatment group | 71 (8 + 8 + 8 + 11 + 10 + 6 + 8 + 6 + 6) | 0 | 0% | 100% |
| IgY antibody treatment group | 6 | 5 | 83.3% | 16.7% |

Note 1:
6 + 5 and 6 + 6 in brackets mean that the test subjects are placed in two pens and represent the number of piglets in each pen; and (8 + 8 + 8 + 11 + 10 + 6 + 8 + 6 + 6) mean that the test subjects are placed in 9 pens and represent the number of piglets in each pen.
Note 2:
test observation was carried out for 72 h, the mortality rate was calculated basedon the number of piglet deaths at the end of the test, and the effective rate was calculated based on the diarrhea scoring index (Table 2).

(2) Scoring of Clinical Treatment of Epidemic Diarrhea in Diseased Pigs with Epidemic Diarrhea During the clinical treatment of the diseased pigs with epidemic diarrhea, the diarrhea indexes of the diseased pigs in the untreated group (6 pigs), the compound 4 treatment group (8 pigs) and the lgY antibody treatment group (6 pigs) were scored through sampling. The results are as shown in Table 2, all 6 diseased pigs in the untreated group died within 48 h; 5 diseased pigs in the lgY antibody treatment group died within 72 h, and 1 diseased pig's condition gradually alleviated; and 8 diseased pigs in the compound 4 treatment group had significantly alleviated diarrhea 24 h after oral administration, most of the pigs recovered after 48 h, and all of the pigs recovered after 72 h, with a curative ratio of 100%.

TABLE 2

Diarrhea Scoring Index

| | | Time after administration | | | |
|---|---|---|---|---|---|
| Number | | 12 h | 24 h | 48 h | 72 h |
| Untreated group | 1 | 3 | Died | | |
| | 2 | 3 | Died | | |
| | 3 | 3 | 3 | Died | |
| | 4 | 3 | Died | | |
| | 5 | 3 | Died | | |
| | 6 | 3 | Died | | |
| Compound 4 treatment group | 1 | 3 | 2 | 0 | 0 |
| | 2 | 2 | 1 | 0 | 0 |
| | 3 | 3 | 2 | 1 | 0 |
| | 4 | 3 | 2 | 0 | 0 |
| | 5 | 3 | 2 | 1 | 0 |
| | 6 | 3 | 2 | 2 | 0 |
| | 7 | 3 | 2 | 0 | 0 |
| | 8 | 3 | 2 | 0 | 0 |
| IgY treatment group | 1 | 3 | 3 | Died | |
| | 2 | 2 | 3 | 3 | Died |
| | 3 | 3 | 2 | 1 | 0 |
| | 4 | 3 | 3 | Died | |
| | 5 | 3 | 3 | Died | |
| | 6 | 2 | 3 | 1 | Died |

Note:
(Formed manure, 0; thick manure, not formed 1; manure and water separation, 2; watery manure, 3; a score of 0 or 1 is considered as normal; and a score of 2 or 3 is considered as diarrhea).

Example 4: Preparation of Antiviral Preparations or Drugs for Treating Porcine Coronavirus Diseases from Bromophenol-Pyrazoline Compounds The bromophenol-pyrazoline compounds in the above Examples 1-2 can be prepared into antiviral preparations that inhibit virus replication, or used as active ingredients in combination with pharmaceutically acceptable carriers to prepare pharmaceutical compositions.

In the antiviral preparations or pharmaceutical compositions, the active ingredient may be a single compound or a mixture of more than two of the above compounds, and can be made into any dosage form as required.

The above description only refers to preferred examples of the present application and is not intended to limit the present application. For those skilled in the art, various alterations and changes can be made to the present application. Any modification, equivalent replacement, improvement and the like made within the sprit and principle of the present application shall be included within the protection scope of the present application.

The invention claimed is:

1. A method for treating porcine coronavirus diseases, said method comprising administering to a subject in need thereof an effective amount of a bromophenol-pyrazoline compound, wherein the bromophenol-pyrazoline compound is 2. The method according to claim 1, wherein the porcine coronavirus diseases are diseases caused by porcine transmissible gastroenteritis virus, porcine epidemic diarrhea virus, porcine respiratory coronavirus, porcine deltacoronavirus and/or porcine hemagglutinating encephalomyelitis virus.

3. The method according to claim 1, wherein the porcine coronavirus diseases include porcine gastroenteritis, diarrhea, respiratory inflammation and/or encephalomyelitis.

* * * * *